(12) United States Patent
Francis

(10) Patent No.: US 7,976,579 B2
(45) Date of Patent: Jul. 12, 2011

(54) RATCHETING NUCLEUS REPLACEMENT

(75) Inventor: Tom Francis, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1219 days.

(21) Appl. No.: 11/621,645

(22) Filed: Jan. 10, 2007

(65) Prior Publication Data
US 2008/0167719 A1 Jul. 10, 2008

(51) Int. Cl.
A61F 2/44 (2006.01)
(52) U.S. Cl. .................. 623/17.11; 623/17.16
(58) Field of Classification Search .... 623/17.11–17.16; 606/246
See application file for complete search history.

(56) References Cited

U.S. PATENT DOCUMENTS

| | | | | |
|---|---|---|---|---|
| 3,986,383 A * | 10/1976 | Petteys | ............................. | 72/393 |
| 5,059,193 A * | 10/1991 | Kuslich | .......................... | 606/247 |
| 5,390,683 A * | 2/1995 | Pisharodi | ...................... | 128/898 |
| 5,693,100 A * | 12/1997 | Pisharodi | ................... | 623/17.16 |
| 5,723,013 A * | 3/1998 | Jeanson et al. | ............. | 623/17.16 |
| 5,782,832 A * | 7/1998 | Larsen et al. | .............. | 623/17.11 |
| 6,022,352 A * | 2/2000 | Vandewalle | .................... | 606/286 |
| 6,127,597 A * | 10/2000 | Beyar et al. | ................. | 606/86 R |
| 6,193,757 B1 * | 2/2001 | Foley et al. | ................ | 623/17.16 |
| 6,332,895 B1 * | 12/2001 | Suddaby | ..................... | 623/17.11 |
| 6,491,724 B1 * | 12/2002 | Ferree | ......................... | 623/17.11 |
| 6,743,255 B2 * | 6/2004 | Ferree | ......................... | 623/17.11 |
| 6,863,673 B2 * | 3/2005 | Gerbec et al. | ................... | 606/99 |
| 6,866,682 B1 * | 3/2005 | An et al. | ..................... | 623/17.15 |
| 7,214,243 B2 * | 5/2007 | Taylor | ......................... | 623/17.11 |
| 7,655,046 B2 * | 2/2010 | Dryer et al. | ................. | 623/17.15 |
| 7,666,209 B2 * | 2/2010 | Zucherman et al. | ......... | 606/249 |
| 7,674,296 B2 * | 3/2010 | Rhoda et al. | ............... | 623/17.15 |
| 7,727,279 B2 * | 6/2010 | Zipnick et al. | ............. | 623/17.11 |
| 7,731,751 B2 * | 6/2010 | Butler et al. | ............... | 623/17.11 |
| 2005/0209696 A1 * | 9/2005 | Lin et al. | ..................... | 623/17.12 |
| 2005/0278036 A1 * | 12/2005 | Leonard et al. | ............ | 623/23.47 |
| 2006/0136062 A1 * | 6/2006 | DiNello et al. | ............ | 623/17.14 |
| 2006/0241770 A1 * | 10/2006 | Rhoda et al. | ............... | 623/17.15 |
| 2006/0276899 A1 * | 12/2006 | Zipnick et al. | ............. | 623/17.13 |
| 2008/0021555 A1 * | 1/2008 | White et al. | ............... | 623/17.11 |
| 2008/0058938 A1 * | 3/2008 | Mujwid | ..................... | 623/17.13 |

* cited by examiner

Primary Examiner — Eduardo C Robert
Assistant Examiner — Ellen C Hammond

(57) ABSTRACT

An intervertebral disc augmentation implant for implantation between a pair of vertebral bodies comprises a core member having a first height dimension along an axis defined by the pair of vertebral bodies and a cavity running perpendicular to the axis, a first post and a second post each having a bottom portion with a plurality of teeth, and a plug having a tapered portion with engaging mechanisms that are configured to mate with the bottom portions of the first and second post. The first and second posts are disposed substantially in the center of the core member along the axis. The bottom portions of the first and second post extend into the cavity at opposite sides of the cavity. The plug is inserted and advanced in the cavity between the bottom portions of the first and second post, thereby expanding the core member from the first height dimension to a second height dimension.

3 Claims, 3 Drawing Sheets

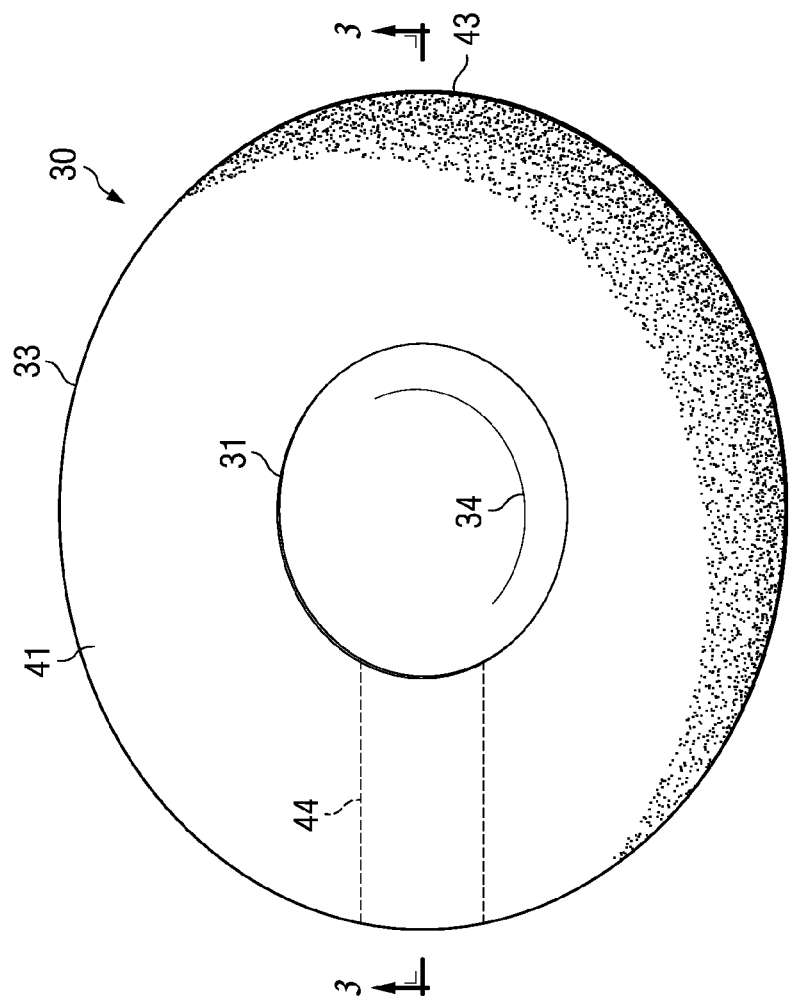
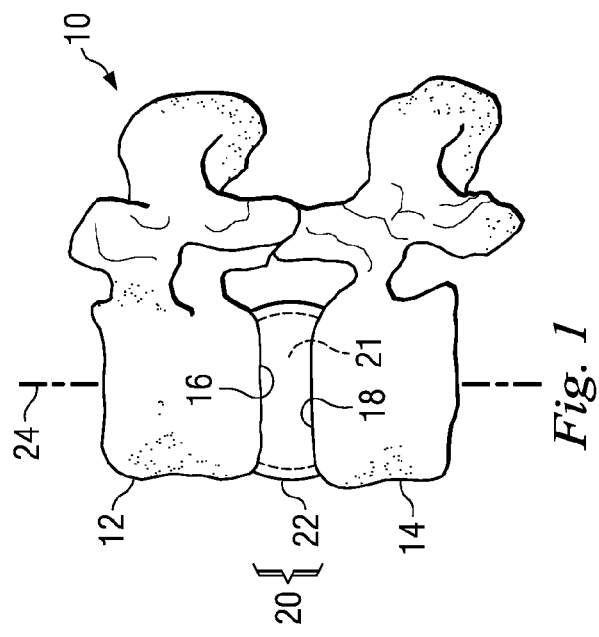

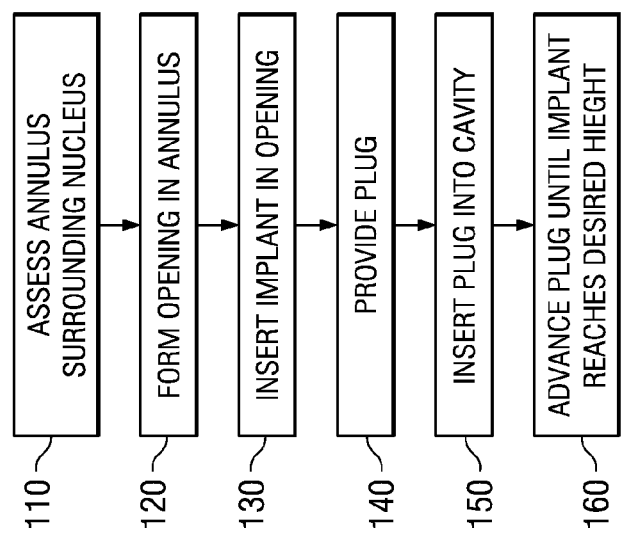
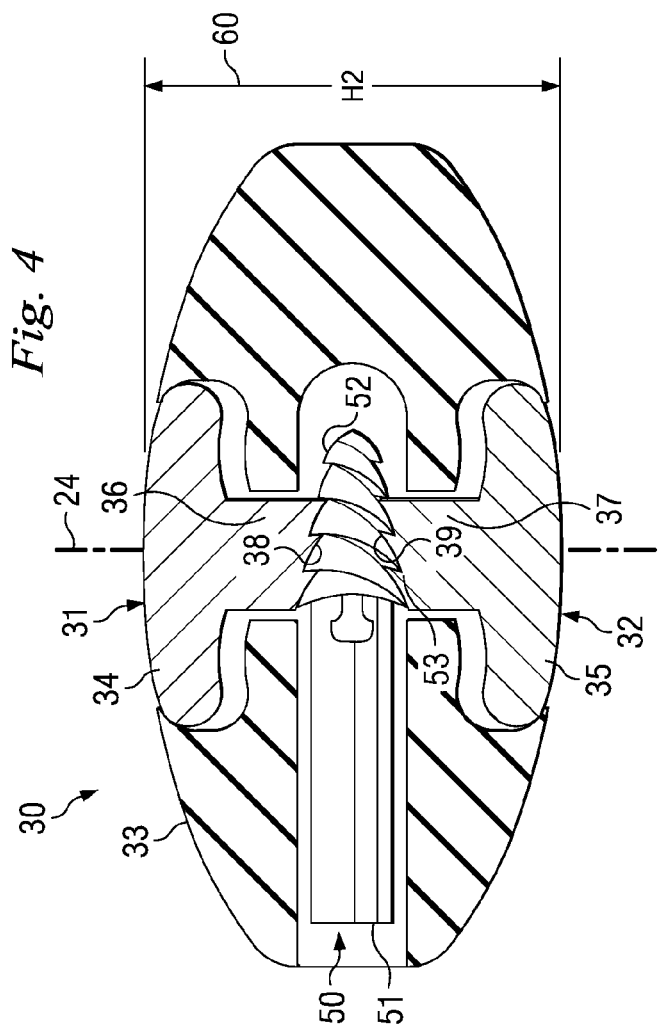

RATCHETING NUCLEUS REPLACEMENT

BACKGROUND

Within the spine, the intervertebral disc functions to stabilize and distribute forces between vertebral bodies. The intervertebral disc comprises a nucleus pulposus which is surrounded and confined by the annulus fibrosis.

Intervertebral discs are prone to injury and degeneration. For example, herniated discs typically occur when normal wear, or exceptional strain, causes a disc to rupture. Degenerative disc disease typically results from the normal aging process, in which the tissue gradually loses its natural water and elasticity, causing the degenerated disc to shrink and possibly rupture.

Intervertebral disc injuries and degeneration may be treated by fusion of adjacent vertebral bodies or by replacing the intervertebral disc with a prosthetic. To maintain as much of the natural tissue as possible, the nucleus pulposus may be supplemented or replaced while maintaining all or a portion of the annulus. A need exists for nucleus replacement and augmentation implants that will reduce the required incision into the annulus.

SUMMARY

In one embodiment, an intervertebral disc augmentation implant for implantation between a pair of vertebral bodies comprises a core member having a first height dimension along an axis defined by the pair of vertebral bodies and a cavity running perpendicular to the axis, a first post and a second post each having a bottom portion with a plurality of teeth, and a plug having a tapered portion with engaging mechanisms that are configured to mate with the bottom portions of the first and second post. The first and second posts are disposed substantially in the center of the core member and along the axis. The bottom portions of the first and second post extend into the cavity at opposite sides of the cavity. The plug is configured to be inserted and advanced in the cavity between the bottom portions of the first and second post, thereby expanding the core member from the first height dimension to a second height dimension.

In some embodiments, the core member has a curved upper surface, a curved lower surface, and a cylindrical side surface. In other embodiments, the cavity has a cylindrical shape and the cavity extends from outside the side surface and passes through the center of the core member. In other embodiments, the first and second posts each comprise of a top portion that is configured to match with endplates of the pair of vertebral bodies and the top portions partly extending outside the curved upper and lower surfaces, respectively. In still other embodiments, the core member is formed of an elastic polymer. In some embodiments, the plug comprises a cylindrical body formed of the same material as the core member and molded to the tapered portion. The cylindrical body is configured to fill the cavity when the plug is inserted and advanced in the cavity.

In other embodiments, the first and second posts are formed of a metal. In other embodiments, the first and second posts are formed of a plastic. In some embodiments, the tapered portion of the plug is formed of the same material as the first and second posts. In still other embodiments, the plurality of teeth of the bottom portions of the first and second post are sloped to allow movement of the plug in one direction.

In another embodiment, a method of replacing a nucleus of an intervertebral disc located between a pair of vertebral bodies comprises accessing an annulus surrounding the nucleus and forming an opening in the annulus. The method further comprises inserting an intervertebral nucleus replacement implant. The implant comprises a core member having a first height dimension along an axis defined by the pair of vertebral bodies and a cavity running perpendicular to the axis, a first post and a second post each having a bottom portion with a plurality of teeth. The first and second posts are disposed substantially in the center of the core member along the axis with the bottom portions of the first and second post extending into the cavity at opposite sides of the cavity. The method further comprises providing a plug having a tapered end with engaging mechanisms that are configured to mate with the bottom portions of the first and second post and inserting the plug into the cavity with the tapered end in first and advancing the plug between the bottom portions of the first and second post until the core member expands from the first height dimension to a second height dimension.

In some embodiments, the method further comprises removing at least a portion of the nucleus through the opening in the annulus. In other embodiments, the step of inserting the implant further comprises placing the implant in contact with at least a portion of the nucleus.

In still another embodiment, an implant for replacing at least a portion of a nucleus of an intervertebral disc between a pair of vertebral bodies comprises a first post and a second post each having a bottom portion with a plurality of teeth. The first and second posts are positioned along an axis defined by the pair of vertebral bodies with the bottom portions facing each other. The implant further comprises a core member surrounding the first and second posts and having a cavity running perpendicular to the axis, and an insert having a tapered portion with engaging mechanisms configured to allow for ratcheting with the bottom portions of the first and second post. The bottom portions of the first and second posts extend into the cavity of the core member. The insert is advanced in the cavity between the bottom portions of the first and second post, thereby expanding the implant to a desired height.

In some embodiments, the first and second posts each comprise of a top portion having a spherical shape to match with endplates of the pair of vertebral bodies, respectively. In other embodiments, the insert further comprises a body portion that is formed of the same material as the core member and configured to fill the cavity when the plug is inserted and advanced in the cavity of the core member. In still other embodiments, the tapered portion of the insert is formed of the same material as the first and second posts and the body portion is molded to the tapered portion. In some embodiments, the cavity extends from outside of the core member and passes through the center of the core member. In other embodiments, the plurality of teeth of the bottom portions of the first and second post are sloped to allow movement of the insert in one direction.

Additional embodiments are included in the attached drawings and the description provided below.

BRIEF DESCRIPTION OF THE DRAWINGS

FIG. 1 is a sagittal view of a section of a vertebral column.

FIG. 2 is a top view of an implant with a core member having a cavity according to one embodiment of the present disclosure.

FIG. 4 is a side cross sectional view of the implant of FIG. 2 and the plug that has been inserted and advanced in the cavity of the implant.

FIG. 5 is a flow chart for a method of replacing a nucleus of an intervertebral disc located between a pair of vertebral bodies.

DETAILED DESCRIPTION

Figure 3:
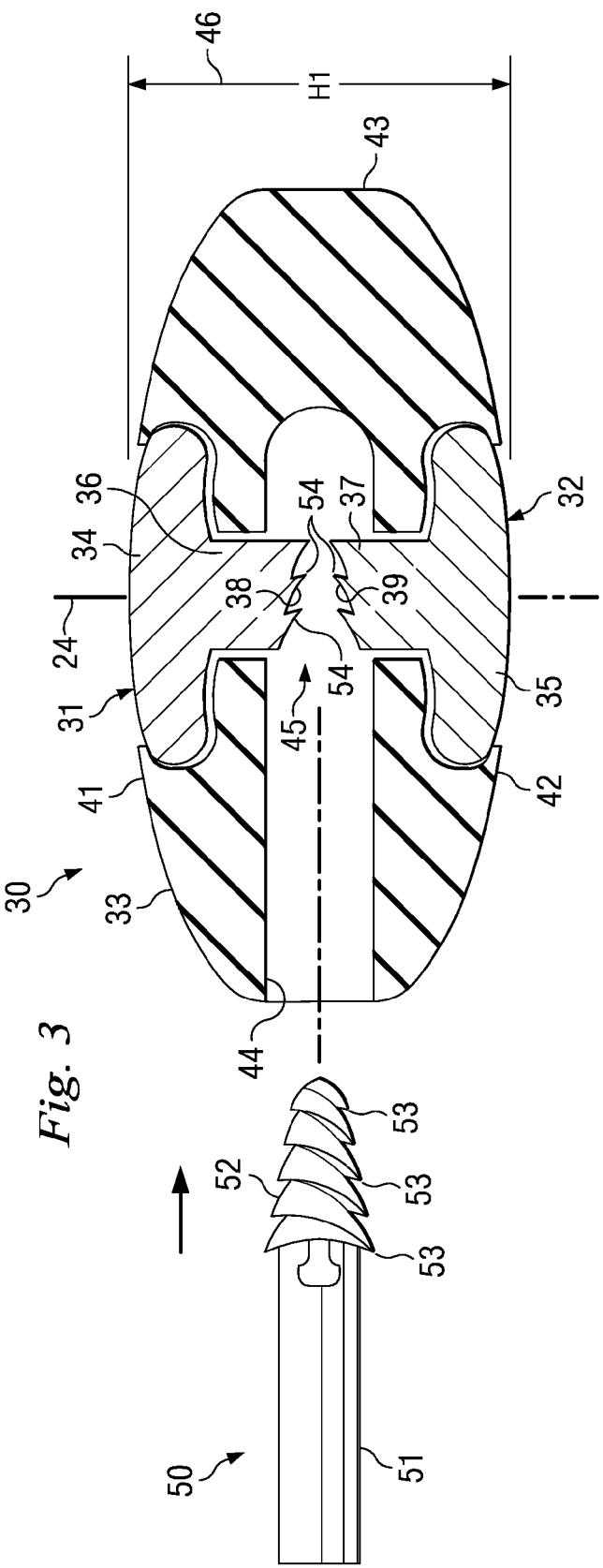
FIG. 3 is a side cross sectional view of the implant of FIG. 2 and a plug for inserting into the cavity of the implant.

The present disclosure relates generally to devices and methods for relieving disc degeneration or injury, and more particularly, to devices and methods for augmenting a nucleus pulposus. For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring first to FIG. 1, the reference numeral 10 refers to a vertebral joint section or a motion segment of a vertebral column. The joint section 10 includes adjacent vertebral bodies 12, 14. The vertebral bodies 12, 14 include endplates 16, 18, respectively. An intervertebral disc space 20 is located between the endplates 16, 18, and an annulus fibrosis 22 surrounds the space 20. In a healthy joint, the space 20 contains a nucleus pulposus 21. The nucleus pulposus 21 may degenerate with age, disease, or trauma. A central longitudinal axis 24 may extend through the vertebral joint 10.

Referring now also to FIGS. 2 and 3, illustrated are top and cross sectional views of a nucleus implant 30 that may be used to augment the function and the existing tissue of the nucleus 21 or may be used to replace all or a portion of the nucleus 21. Thus, the implant 30 may fill all or a portion of the disc space 20 within the annulus 22. The implant 30 may comprise of a first post 31 and a second post 32 that are surrounded by a core member 33. The first post 31 and second post 32 may be disposed substantially in the center of the core member 33 along the central longitudinal axis 24.

The first and second posts 31, 32 may each comprise of a top portion 34, 35 and a bottom portion 36, 37, respectively. The top portions 34, 35 may partly extend outside the core member 33 and may be configured to match with the endplates 16, 18 of the pair of vertebral bodies 12, 14. For example, the top portions 34, 35 may have a spherical shape and/or curved surface to cooperate with the endplates 16, 18, respectively.

The bottom portions 36, 37 may be completely surrounded by the core member 33 and may be positioned such that they face each other as shown. The bottom portions 36, 37 may each have a cylindrical shape with a bottom surface having ridges or outwardly protruding teeth 38, 39. As can be seen, the outwardly protruding teeth 38, 39 are formed as triangular shaped protrusions. However, other shapes of the outwardly protruding teeth 38, 39 may be used including for example, frustums, rounded, truncated, sinusoidal shaped teeth, among others.

The first and second posts 31, 32 may be formed of a metal. Suitable metals may include, but are not limited to, cobalt-chrome alloys, titanium, titanium alloys, stainless steel, or titanium nickel alloys. Alternatively, the first and second posts 31, 32 may be optionally formed of a plastic such as polyetheretherketone (PEEK) or PEEK composites. The first and second posts 31, 32 may also be formed of other suitable materials that are rigid enough to adequately provide for vertebral support.

The core member 33 may comprise of a curved upper surface 41, a curved lower surface 42, and a cylindrical side surface 43. The curved upper and lower surfaces 41, 42 may have an opening for the top portions 34, 35 of the first and second posts 31, 32, respectively. The core member 33 may also comprise of a cavity 44 that runs perpendicular to the central longitudinal axis 24 and extends from outside the cylindrical side surface 43 and passes through the center of the core member 33. The cavity 44 may have a cylindrical shape. Alternatively, the cavity 44 may optionally be tubular having a substantially square cross section. It is understood that the cross section of the cavity 44 may include other shapes such as oval or other polygons. The bottom portions 36, 37 of the first and second post 31, 32 may extend into the cavity 44 at opposites sides of the cavity such that the protruding teeth 38, 39 face each other and define a space 45 within the cavity 44. The core member 33 may initially have a first height dimension 46 defined along the central longitudinal axis 24.

The core member 33 may be formed of an elastic polymer. Suitable polymers may include, but are not limited to, BIONATE® polycarbonate-urethane, PURSIL™ silicone-polyetherurethane, ultra-high molecular weight polyethylene (UHMWPE), polyurethane, silicone-polyurethane copolymers, or polymethylmethacrylate. Additionally, the core member 33 may include a radiocontrast marker or material such as barium sulfate, tungsten, tantalum, or titanium for purposes of viewing the implant 30 with imaging equipment.

In FIG. 3, also illustrated is a cross sectional view of a plug or insert 50 for inserting into the cavity 44 of the core member 33. The plug 50 may comprise of a body portion 51 and a tapered portion 52. The body portion 51 may be formed of the same material as the core member 33. The body portion 51 may be configured and shaped to fill in the cavity 44 when the plug 50 is inserted into the cavity. The body portion 51 may have a cylindrical shape. Alternatively, the body portion 51 may optionally be tubular having a substantially square cross section.

The tapered portion 52 may be formed of the same material as the first and second posts 31, 32. The tapered portion 52 may comprise of engaging mechanisms, such as teeth 53, that are configured to mate with the protruding teeth 38, 39 of the first and second post 31, 32. Accordingly, the configuration of the engaging mechanisms of the tapered portion 52 will depend on type of protruding teeth 38, 39 that are used for the first and second posts 31, 32. The space 45 defined by the protruding teeth 38, 39 may comprise of notches 54. The notches 54 engage and mate with the engaging mechanisms 53 of the tapered portion 52 as will be discussed below. The body portion 51 may be molded to the tapered portion 52.

Referring now also to FIG. 4, illustrated is a cross sectional view of the nucleus implant 30 with the plug 50 inserted and advanced in the cavity 44. As previously noted, the core member 33 may initially have a first height dimension 46 defined along the central longitudinal axis 24 (FIG. 3). The plug 50 may be inserted into the cavity 44 with the tapered portion 52 in first. As the plug 50 approaches the space 45 defined by the bottom portions 36, 37, the teeth 53 of the tapered portion 52 begin to engage and mate with the notches 54 defined by the protruding teeth 38, 39. As the plug 50 is further advanced in the cavity 44, the teeth 53 of the tapered portion 52 disengage and then engage with the notches 54, thereby ratcheting between the protruding teeth 38, 39 of the bottom portions 36, 37.

The protruding teeth 38, 39 of the bottom portions 36, 37 may be sloped to allow for ratcheting in one direction with the tapered portion 52. That is, the plug 50 may be allowed to move in one direction after the teeth 53 of the tapered portion 52 begin to mate with the notches 54 defined by the protruding teeth 38, 39 of the bottom portions 36, 37. As a result, the plug 50 is securely held or positioned in the cavity 44 and may only be advanced (in one direction) by ratcheting the tapered portion 52 to the next set of notches 54. Additionally, the teeth 53 of the tapered portion 52 increase in width as the plug 50 is advanced in the cavity 44. Accordingly, the first and second posts 31, 32 are forced apart, thereby expanding the core member 33 from the first height dimension 46 to a second height dimension 60. This allows the implant 30 to be expanded to a desired height in the disc space 20 between the pair of vertebral bodies 12, 14.

The core member 33 described above may assume any of a variety of three-dimensional shapes including spherical, elliptoid, boomerang, disc, capsule, kidney, or cylindrical. Furthermore, the core members in the embodiments described above may be uniform, non-composite structures and may have isotropic material properties throughout the core member. Composite structures, such as layered structures, having anisotropic material properties may also be suitable.

Referring now also to FIG. 5, illustrated is a flow chart for a method 100 of replacing a nucleus 21 of an intervertebral disc 20 located between a pair of vertebral bodies 12, 14. The method 100 begins with step 110 in which an annulus 22 surrounding the nucleus 21 may be assessed. Prior to positioning any of the implants described above in the intervertebral disc space 20, an incision may be made in the annulus fibrosis or an existing annulus defect may be identified. The annulus 22 may be accessed through a posterior, lateral, anterior, or any other suitable approach.

In one embodiment, a guide wire or other small instrument may be used to make the initial hole. If necessary, successively larger holes are cut from an initially small puncture. The hole (also called an aperture, an opening, or a portal, for example) may be as small as possible to minimize expulsion of the material through the hole after the surgery is complete. Also if necessary, a dilator may be used to dilate the hole, making it large enough to deliver the implant to replace or augment the disc nucleus. The dilator may stretch the hole temporarily and avoid tearing so that the hole can return back to its undilated size after the instrument is removed. Although some tearing or permanent stretching may occur, the dilation may be accomplished in a manner that allows the hole to return to a size smaller than its dilated size after the surgery is complete. In alternative embodiments, portions of the annulus 22 may be resected to allow passage of the implants.

The method 100 continues with step 120 in which an opening is formed in the annulus 22. Through the annulus opening, all or a portion of the natural nucleus pulposus 21 may be removed. Any of a variety of tools may be used to prepare the disc space 20, including specialized pituitary rongeurs and curettes for reaching the margins of the nucleus pulposus. Ring curettes may be used to scape abrasions from the vertebral endplates as necessary. Using these instruments, a centralized, symmetrical space large enough to accept the implant footprint may be prepared in the disc space 20. It is understood that the natural nucleus pulposus need not be removed, but rather, an implant of the type described above may be used in cooperation with existing nucleus tissue to compensate for deficiencies in the existing tissue. The disc space 20 may then be distracted to a desired level by distractors or other devices known to the skilled artisan for such purposes.

The method 100 continues with step 130 in which, after preparing the disc space 20 and/or annulus 22 for receiving an implant, the implant may be delivered into the intervertebral disc space using any of a variety of techniques known in the art. The implant 30 of FIG. 2 may be employed. As previously discussed, the implant 30 comprises a core member 33 having a cavity 44, and first and second posts 31, 32 each having a bottom portion 36, 37 with protruding teeth 38, 39. The core member 33 initially has a first height dimension 45 when delivered into the disc space 20. Accordingly, this reduces the incision that is required to receive the implant 30 into the disc space 20.

The method 100 continues with step 140 in which a plug for inserting into the cavity 44 of the core member 33 is provided. The plug 50 of FIG. 3 may be employed. As previously discussed, the plug 50 may comprise of a body portion 51 and a tapered portion 52. The tapered portion 52 may comprise of teeth 53 that are configured to mate with the protruding teeth 38, 39 of the bottom portions 36, 37 of the first and second post 31, 32.

The method 100 continues with step 150 in which the plug 50 is inserted into the cavity 44 with the tapered portion 52 in first. The teeth 53 of the tapered portion 52 of the plug 50 may begin to engage and mate with the bottom portions 36, 37 of the first and second post 31, 32 that extend into the cavity 44.

The method 100 continues with step 160 in which the plug 50 is advanced in the cavity 44 until the implant 30 reaches a desired height in the disc space 20. The teeth 53 of the tapered portion 52 are ratcheted between the protruding teeth 38, 39 of the bottom portions 36, 37 as the plug 50 is advanced in the cavity 44 in one direction. The plug 50 is securely held in place by the notches 54 defined by the protruding teeth 38, 39. Accordingly, the first and second posts 31, 32 expand and engage towards inferior and superior endplates 16, 18 of the pair of vertebral bodies 12, 14, respectively. As a result, the core member 33 expands from the first height dimension to a second height dimension. Thus, the plug 50 is ratcheted and advanced in the cavity 44 until the implant 30 reaches the desired height in the disc space 20.

Although only a few exemplary embodiments have been described in detail above, those skilled in the art will readily appreciate that many modifications are possible in the exemplary embodiments without materially departing from the novel teachings and advantages of this disclosure. For example, the annulus may be partially or completely removed and may be replaced with an artificial device to cooperate and function with the nucleus implants disclosed herein. Accordingly, all such modifications and alternatives are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "anterior," "posterior," "superior," "inferior," "upper," and "lower" are for illustrative purposes only and can be varied within the scope of the disclosure. In the claims, means-plus-function clauses are intended to cover the elements described herein as performing the recited function and not only structural equivalents, but also equivalent elements.

What is claimed is:

1. An intervertebral disc augmentation implant for implantation between a pair of vertebral bodies comprising:
a core member having a first height dimension along an axis defined by the pair of vertebral bodies and a cavity running perpendicular to the axis, wherein the core member is formed of an elastic polymer;
a first post and a second post each having a top portion and a bottom portion, each bottom portion having a plurality of teeth, the first and second posts are disposed substantially in the center of the core member along the axis, the bottom portions of the first and second post extending into the cavity at opposite sides of the cavity, the top portions each having a spherical shape; and
a plug having a tapered portion with engaging mechanisms that are configured to mate with the plurality of teeth of the bottom portions of the first and second post;
wherein the plug is inserted into the cavity and advanced between the bottom portions of the first and second post, thereby expanding the core member from the first height dimension to a second height dimension, wherein the plug further comprises a cylindrical body formed of the same material as the core member and molded to the tapered portion, and wherein the cylindrical body is configured to fill the cavity when the plug is inserted and advanced in the cavity of the core member.

2. An implant for replacing at least a portion of a nucleus of an intervertebral disc between a pair of vertebral bodies, each vertebral body having respective endplates, the implant comprising:
a first post and a second post each having a top portion and a bottom portion, each bottom portion having a plurality of teeth, the first and second posts positioned along an axis defined by the pair of vertebral bodies with the bottom portions facing each other, each top portion having a curved surface that cooperates with its respective endplate, each top portion having a smooth surface that lacks any protrusions for bone penetration;
a core member surrounding the first and second posts and having a cavity running perpendicular to the axis, the bottom portions of the first and second post extending into the cavity of the core member; and
an insert having a tapered portion with engaging mechanisms configured to allow for ratcheting with the bottom portions of the first and second post;
wherein the insert is advanced in the cavity between the bottom portions of the first and second post, thereby expanding the implant to a desired height, wherein the insert further comprises a body portion that is formed of the same material as the core member and configured to fill the cavity when the plug is inserted and advanced in the cavity of the core member.

3. The implant of claim 2, wherein the tapered portion of the insert is formed of the same material as the first and second posts and wherein the body portion is molded to the tapered portion.

* * * * *

UNITED STATES PATENT AND TRADEMARK OFFICE
CERTIFICATE OF CORRECTION

| | | |
|---|---|---|
| PATENT NO. | : 7,976,579 B2 | Page 1 of 1 |
| APPLICATION NO. | : 11/621645 | |
| DATED | : July 12, 2011 | |
| INVENTOR(S) | : Francis | |

It is certified that error appears in the above-identified patent and that said Letters Patent is hereby corrected as shown below:

In Fig. 5, Sheet 3 of 3, for Tag "160", Line 2, delete "HIEGHT" and insert -- HEIGHT --, therefor.

In Column 5, Line 20, delete "elliptoid," and insert -- ellipsoid, --, therefor.

In Column 5, Line 60, delete "scape" and insert -- scrape --, therefor.

Signed and Sealed this
Twenty-third Day of August, 2011

David J. Kappos
*Director of the United States Patent and Trademark Office*